(12) United States Patent
Houjou et al.

(10) Patent No.: US 10,542,928 B2
(45) Date of Patent: Jan. 28, 2020

(54) MEDICAL IMAGING DEVICE INCLUDING FIRST AND SECOND LIGHT SOURCES HAVING DIFFERENT LIGHT EMISSION DIRECTIONS

(71) Applicant: CASIO COMPUTER CO., LTD., Shibuya-ku, Tokyo (JP)

(72) Inventors: Yoshiharu Houjou, Tokyo (JP); Jumpei Ishibashi, Nishi Tokyo (JP); Katsuyuki Matsuo, Hanno (JP); Nobuhiro Aoki, Kokubunji (JP)

(73) Assignee: CASIO COMPUTER CO., LTD., Tokyo (JP)

( * ) Notice: Subject to any disclaimer, the term of this patent is extended or adjusted under 35 U.S.C. 154(b) by 0 days.

(21) Appl. No.: 15/926,221

(22) Filed: Mar. 20, 2018

(65) Prior Publication Data

US 2018/0279942 A1    Oct. 4, 2018

(30) Foreign Application Priority Data

Apr. 4, 2017    (JP) ................................. 2017-074362
Feb. 16, 2018   (JP) ................................. 2018-026288

(51) Int. Cl.
*H04N 5/232* (2006.01)
*A61B 5/00* (2006.01)

(52) U.S. Cl.
CPC ............ *A61B 5/444* (2013.01); *A61B 5/0064* (2013.01); *A61B 5/0077* (2013.01); *A61B 5/0075* (2013.01);
(Continued)

(58) Field of Classification Search
CPC ..... A61B 5/444; A61B 5/0077; A61B 5/0064; A61B 5/443; A61B 5/0082; A61B 5/0075; H04N 5/23229
See application file for complete search history.

(56) References Cited

U.S. PATENT DOCUMENTS 7,006,223 B2   2/2006   Mullani
7,369,692 B2   5/2008   Shirai et al.
(Continued)

FOREIGN PATENT DOCUMENTS

JP      10333057 A     12/1998
JP      2002014289 A    1/2002
(Continued)

OTHER PUBLICATIONS

Extended European Search Report (EESR) dated Aug. 17, 2018 issued in counterpart European Application No. 18163499.9.

*Primary Examiner* — Hung H Lam
(74) *Attorney, Agent, or Firm* — Holtz, Holtz & Volek PC

(57) ABSTRACT

A medical imaging device changes a state between a first capturing state for capturing a lesion in a regular capturing state and a second capturing state for capturing a lesion in a capturing state that is different from the regular capturing state and captures an image for assisting in diagnosis of the lesion. The medical imaging device includes an imaging device body that includes a first light source, a second light source, an imaging element, a set of lenses that are situated on an optical axis that connects the imaging element and an object, uses at least the first light source as a light source that emits light to the object in the first capturing state, and uses at least the second light source as a light source that emits light to the object in the second capturing state.

13 Claims, 14 Drawing Sheets

(52) U.S. Cl.
CPC .............. *A61B 5/0082* (2013.01); *A61B 5/443* (2013.01); *H04N 5/23229* (2013.01)

(56) References Cited

U.S. PATENT DOCUMENTS

| | | | |
|---|---|---|---|
| 8,162,496 B2 | 4/2012 | Kang et al. | |
| 8,657,739 B2 | 2/2014 | Chen | |
| 9,458,990 B2 | 10/2016 | Mullani | |
| 2003/0026110 A1* | 2/2003 | Satoh | A61B 5/0059 362/572 |
| 2004/0257439 A1* | 12/2004 | Shirai | A61B 5/0059 348/77 |
| 2008/0180950 A1* | 7/2008 | Kang | A61B 5/0059 362/249.16 |
| 2015/0036311 A1 | 2/2015 | Mullani | |

FOREIGN PATENT DOCUMENTS

| | | |
|---|---|---|
| JP | 2003024283 A | 1/2003 |
| JP | 2012148051 A | 8/2012 |

* cited by examiner

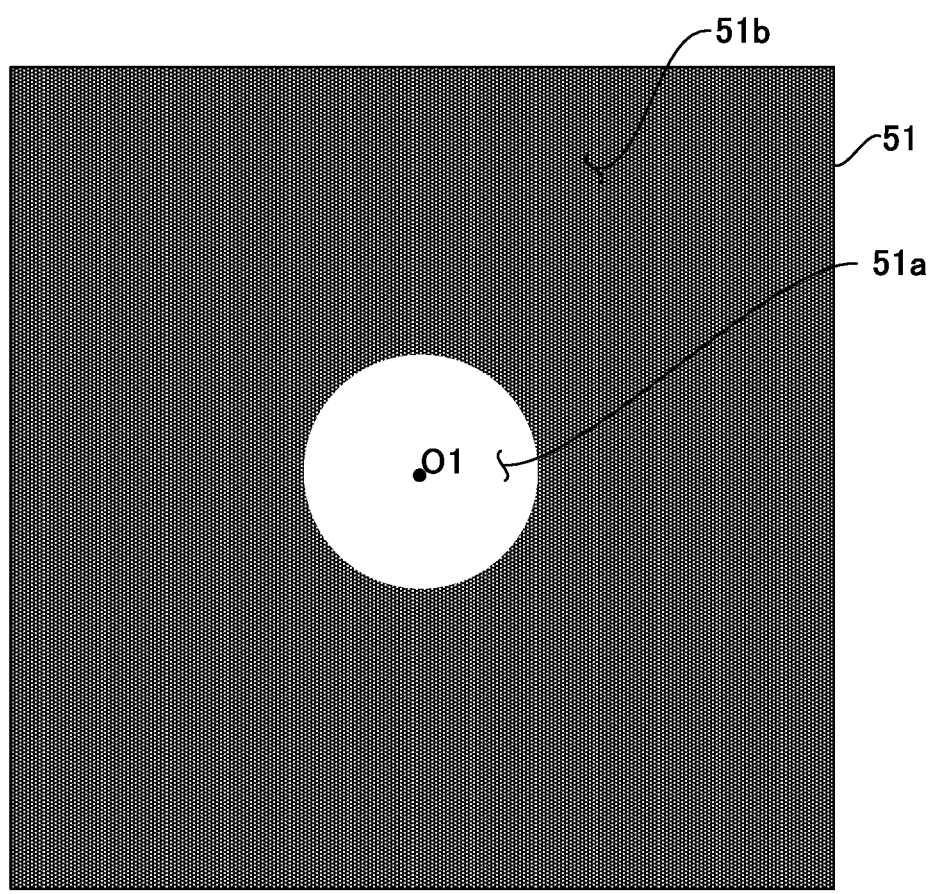

MEDICAL IMAGING DEVICE INCLUDING FIRST AND SECOND LIGHT SOURCES HAVING DIFFERENT LIGHT EMISSION DIRECTIONS

CROSS-REFERENCE TO RELATED APPLICATION

This application claims the benefit of Japanese Patent Application No. 2017-074362, filed on Apr. 4, 2017 and Japanese Patent Application No. 2018-026288, filed on Feb. 16, 2018, the entire disclosure of which is incorporated by reference herein.

FIELD

This application relates generally to a medical imaging device.

BACKGROUND

In these years, increase in skin diseases such as melanoma (melanocarcinoma) due to aging society and ozone depletion is a problem. For diagnosing such skin diseases, a device called dermoscope for viewing the pigment distribution and/or color of the inner skin part is utilized. For example, the dermoscope disclosed in Patent Literature 1: U.S. Pat. No. 7,006,223 is provided with a diode in each of different polarizing filters and can be switched between a state enabling observation of the skin surface and a state enabling observation of the inner skin part by switching the diode to emit light.

SUMMARY

A medical imaging device of the present disclosure is a medical imaging device that changes a state between a first capturing state for capturing a lesion in a regular capturing state and a second capturing state for capturing a lesion in a capturing state that is different from the regular capturing state and captures an image for assisting in diagnosis of the lesion, comprising a first light source and a second light source wherein at least the first light source is used as a light source that emits light to the object in the first capturing state, and at least the second light source is used as a light source that emits light to the object in the second capturing state, and an emission direction of the second light source is set to a direction that is different from an emission direction of the first light source.

BRIEF DESCRIPTION OF THE DRAWINGS

A more complete understanding of this application can be obtained when the following detailed description is considered in conjunction with the following drawings, in which:

FIG. 7A is a schematic illustration that shows the illuminance distribution of light that is emitted by a light source on the illuminated surface shown in FIG. 5;

DETAILED DESCRIPTION

Embodiments of the dermoscopic camera to which the present disclosure is applied will be described below with reference to the drawings. In the specification of the present application, in accordance with usage of the terms "microscope" and "microscopy: examination with a microscope or use (usage) of a microscope," the terms "dermoscope" and "dermoscopy" are used to refer to a magnifier for skin examination (a device) and skin examination with a magnifier or use of a magnifier (a deed).

Embodiment 1

(Overall Configuration of a Dermoscopic Camera 1)

Figure 1:
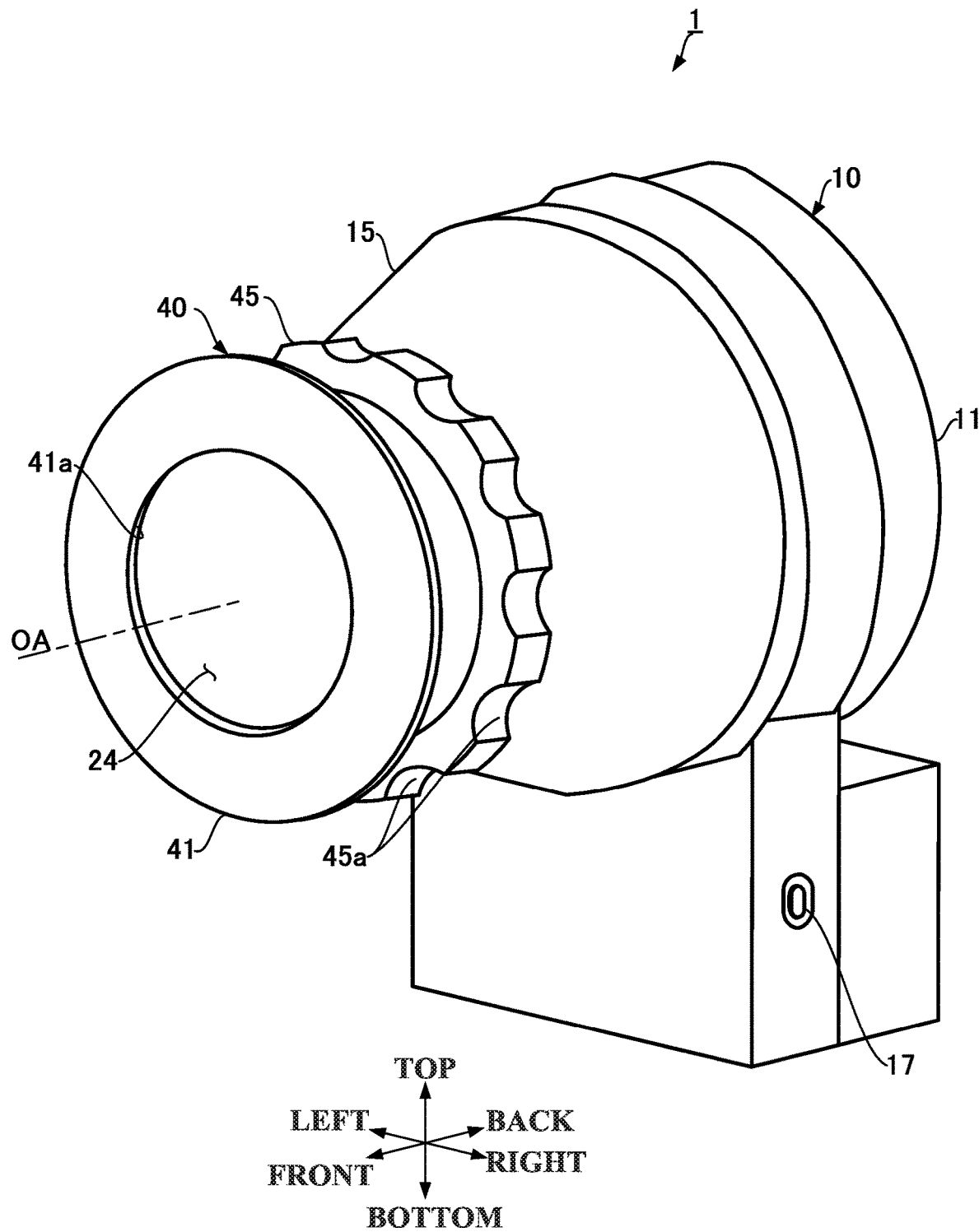
FIG. 1 is a perspective view of a dermoscopic camera of Embodiment 1 to which the present disclosure is applied during dermoscopic capturing.
Figure 2:
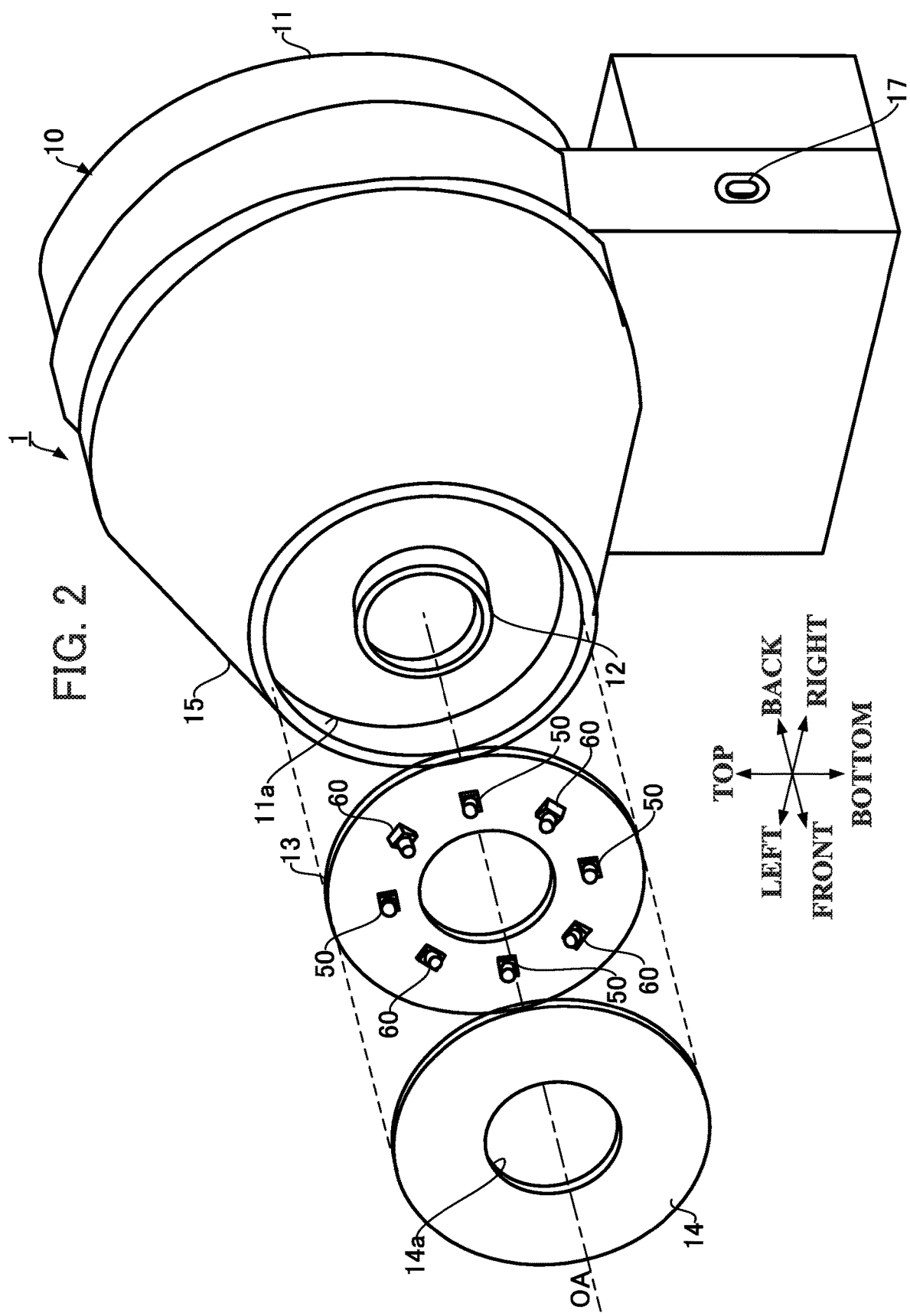
FIG. 2 is an exploded, perspective view of the dermoscopic camera of Embodiment 1 to which the present disclosure is applied during regular capturing.
Figure 3:
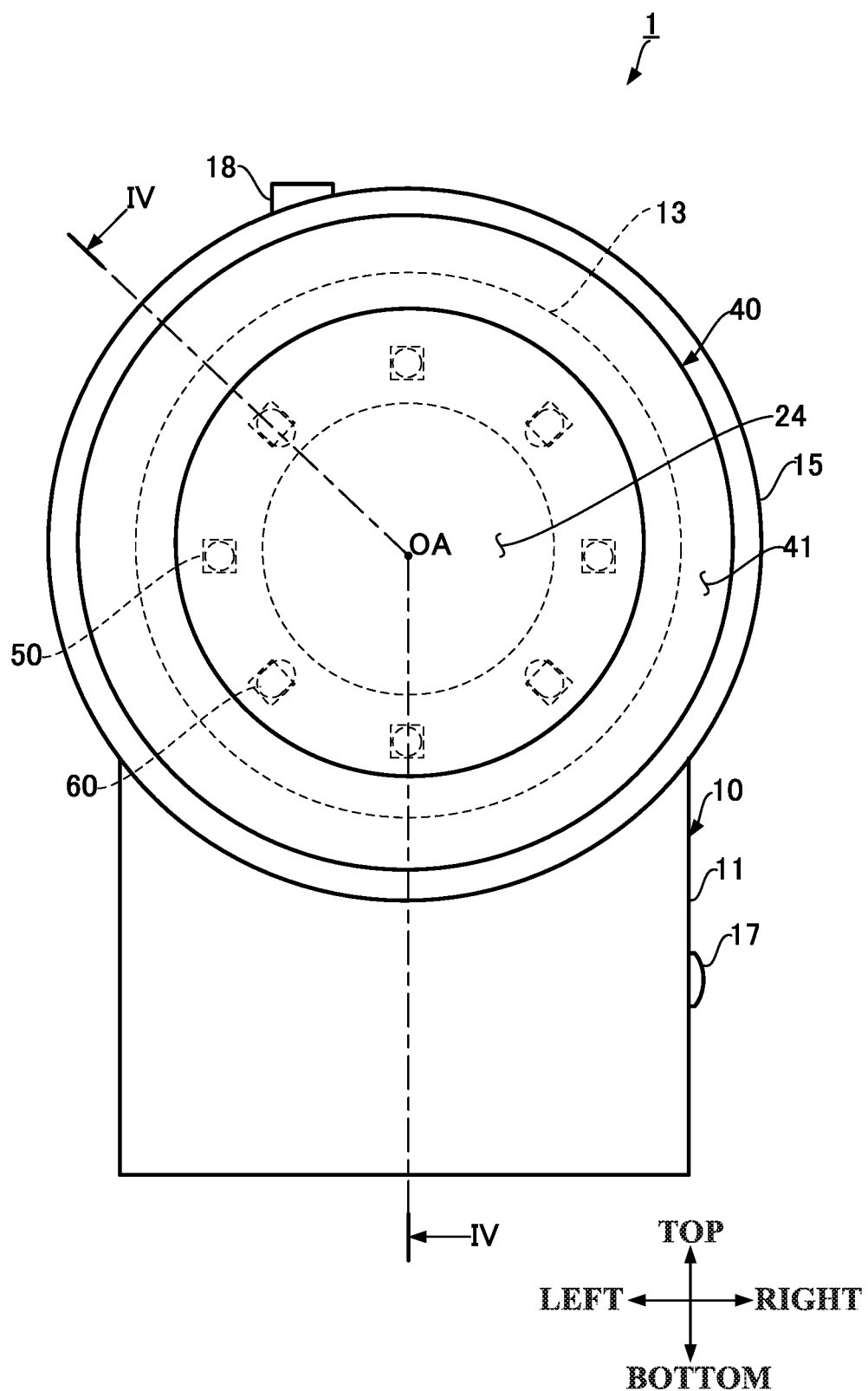
FIG. 3 is a front view of the dermoscopic camera of Embodiment 1 to which the present disclosure is applied.
Figure 4:
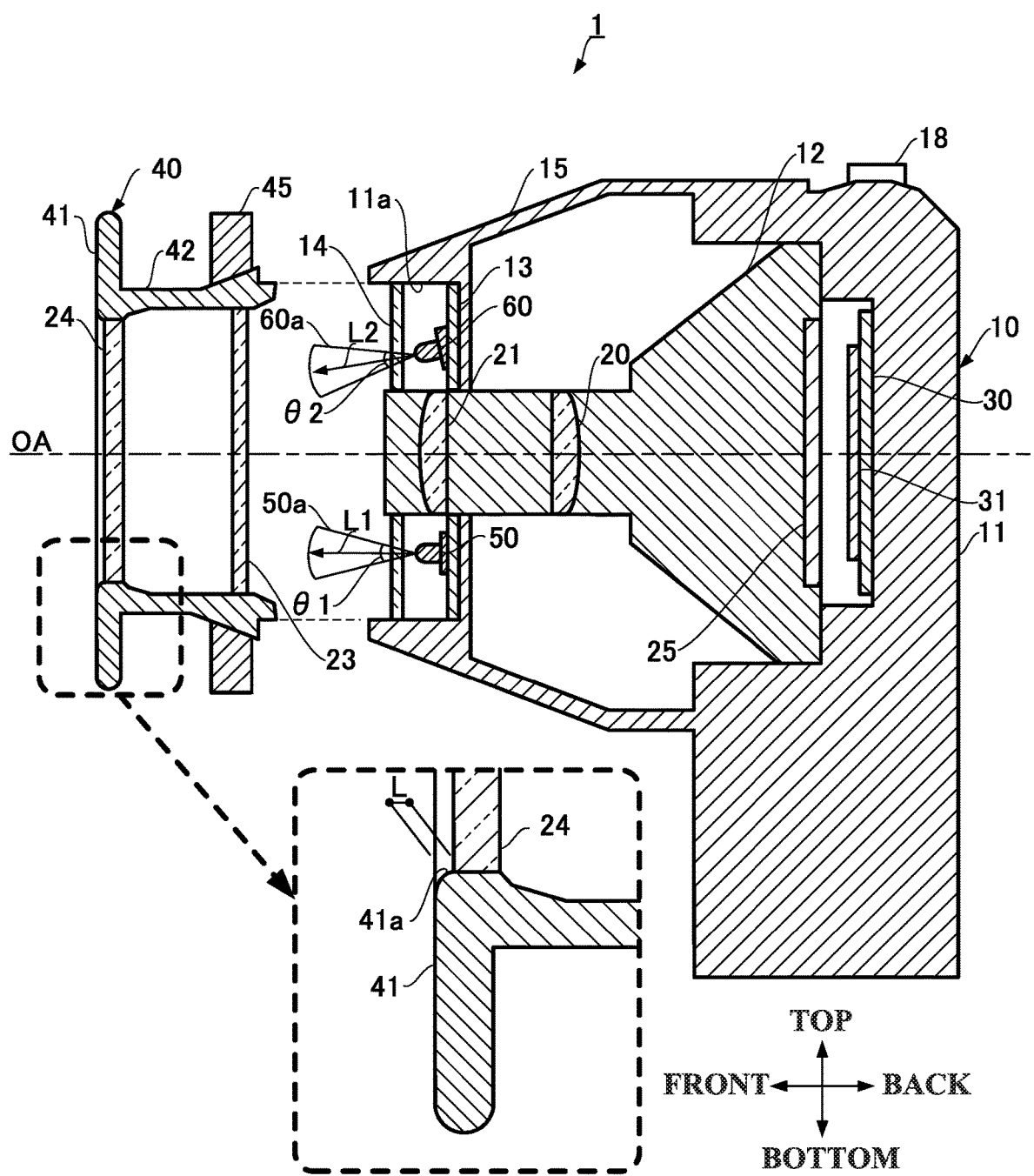
FIG. 4 is an exploded, cross-sectional view of the dermoscopic camera at the section line IV-IV in FIG. 3.

FIG. 1 is a perspective view of a dermoscopic camera of Embodiment 1 to which the present disclosure is applied during dermoscopic capturing. FIG. 2 is an exploded, perspective view of the dermoscopic camera of Embodiment 1 to which the present disclosure is applied during regular capturing. FIG. 3 is a front view of the dermoscopic camera of Embodiment 1 to which the present disclosure is applied. FIG. 4 is an exploded, cross-sectional view of the dermoscopic camera at the section line IV-IV in FIG. 3. As shown in FIGS. 1 to 4, the dermoscopic camera (a medical imaging device) 1 generally comprises a camera body (an imaging device body) 10 and an attachment 40 that is detachably attached to the camera body 10.

The following explanation will be made based on an orthogonal coordinate system as shown in FIG. 1 in which the end to an imaging target (an object) is referred to as the front (the front face) of the dermoscopic camera 1, the end opposite thereto is referred to as the back, and the vertical and horizontal directions when the dermoscopic camera 1 is seen from the front are referred to as the vertical and horizontal directions as they are. Moreover, unless otherwise mentioned, the members are mounted by proper methods such as mounting by screws and vises or mounting by fitting.

The dermoscopic camera 1 can be switched between a dermoscopic capturing state (a first capturing state) in which the attachment 40 is attached to the front of the camera body 10 to enable dermoscopic capturing as shown in FIG. 1 and a regular capturing state (a second capturing state) in which the attachment 40 is detached from the front of the camera body 10 to enable regular capturing as shown in FIG. 2.

Here, the regular capturing means capturing by general camera usage such as capturing the surface of a skin lesion.

(Configuration of the Camera Body 10)

The camera body 10 has an enclosure 11 and houses various components in the enclosure 11, such as a lens unit 12 having a set of lenses and a shutter 25, an LED substrate 13 on which light emitting diodes (LEDs) as a light source are mounted, a cover plate 14, a circuit wiring substrate 30, and an imaging element 31. A shutter button 18 (FIG. 3) is provided on the top surface of the enclosure 11 and a power button 17 is provided on the right face of the same. Moreover, a touch panel screen (not shown) for displaying captured images and executing various settings on the dermoscopic camera 1 is provided to the camera body 10.

Furthermore, a storage that stores captured images that are read by the imaging element 31 according to operation on the shutter button 18, a controller that controls the above-described components, and a battery that supplies electric power to the above-described components are provided in the enclosure 11 although those are not shown in the figures.

A known imaging element can be used as the imaging element 31 and, for example, a charge coupled device (CCD) image sensor or a complementary metal oxide semiconductor (CMOS) image sensor can be used. The camera body 10 can capture an image of an object using the imaging element 31. The camera body 10 can capture, for example, a still image and a video image.

The set of lenses that are possessed by the lens unit 12 is situated on an optical axis OA and includes a first capturing lens 20 and a second capturing lens 21. The first capturing lens 20 and the second capturing lens 21 comprise, for example, planoconvex lenses. The first capturing lens 20 and the second capturing lens 21 are interposed between a skin lesion that is an object and the imaging element 31. As described later, the first capturing lens 20 is movable back and forth. As a result, the focal length changes and the magnification can be altered. Lenses that can together magnify a lesion of a patient 10 to 30 times are used for the first capturing lens 20 and the second capturing lens 21. In other words, the first capturing lens 20 and the second capturing lens 21 function as a wide-angle lens during regular capturing and function as a magnifying lens or a macro lens during dermoscopic capturing.

Moreover, the lens unit 12 includes the shutter 25 that opens/closes for exposure during capturing. Various types of shutters can be used for the shutter 25. The shutter 25 is, for example, a lens shutter or a focal plane shutter. A lens shutter is provided with a small partition that swiftly opens/closes with spring force. The time from the partition completely opening to completely closing is the exposure time (the shutter speed). As the partition closes, the light that has entered the lens unit 12 is blocked by the partition and does not reach the imaging element 31.

The enclosure 11 has a cover part 15 that is tapered to the front and cylindrical. The lens unit 12 is housed in the center of the cover part 15. Moreover, a substrate housing part 11a that is an annular recess is so formed in the enclosure 11 as to surround the lens unit 12. The annular LED substrate 13 on which first LEDs 50 and second LEDs 60 are mounted is housed in the substrate housing part 11a. Moreover, an annular cover plate 14 that covers in front of the LED substrate 13 is provided to the enclosure 11.

Four first LEDs 50 and four second LEDs 60 are mounted on the front face of the LED substrate 13. The LED substrate 13 is so disposed as to surround the vicinity of the second capturing lens 21 that is in the front of the set of lenses. As a result, the first LEDs 50 and the second LEDs 60 are disposed around the set of lenses.

The first LEDs 50 are, for example, bullet-type LEDs and emit a large amount of light in the direction of the bullet-like part protruding. The first LEDs 50 are mounted so that the protruding direction of the bullet-like part is perpendicular to the LED substrate 13 as shown in FIGS. 2 and 4. As a result, the first LEDs 50 are provided to the dermoscopic camera 1 with the bullet-like part protruding in the direction parallel to the optical axis OA and facing forward. The first LEDs 50 that are provided to the dermoscopic camera 1 as described above emit a larger amount of light in the emission direction indicated by the arrow L1 in FIG. 4, namely the forward direction that is the direction parallel to the optical axis OA. Here, the optical axis OA is the axis of symmetry that passes through the center of the optical image formation system and situated on the line that connects the object and the imaging element 31.

Similarly, the second LEDs 60 also comprise bullet-type LEDs. However, the second LEDs 60 are mounted with the protruding direction of the bullet-like part being tilted with respect to the LED substrate 13 as shown in FIGS. 2 and 4. For example, the second LEDs 60 are mounted on the LED substrate 13 with the protruding direction of the bullet-like part being turned to the center of the LED substrate 13 by a specific angle from the state of being mounted perpendicularly to the LED substrate 13. In other words, the second LEDs 60 are mounted with the bullet-like part facing in a direction toward the optical axis OA. As a result, the second LEDs 60 emit a larger amount of light in an emission direction as indicated by the arrow L2 in FIG. 4 that is turned to the center of the LED substrate 13 by a specific angle from the forward direction, namely in a direction of approaching the optical axis OA of the dermoscopic camera 1. As described above, the first LEDs 50 has the emission direction set to the forward direction indicated by the arrow L1 in FIG. 4 (the direction parallel to the optical axis OA). On the other hand, the second LEDs 60 has the emission direction set to a direction that is slightly turned to the center from the forward direction (slightly to the optical axis OA from the forward direction) as indicated by the arrow L2 in FIG. 4. Thus, the emission direction L1 of the first LEDs 50 and the emission direction L2 of the second LEDs 60 are different.

The first LEDs 50 and the second LEDs 60 are disposed at equal intervals on a circle sharing the center with the LED substrate 13 and disposed alternately along the circumferential direction of the circle. The first LEDs 50 and the second LEDs 60 comprise bullet-type LEDs that emit white light. As described later, the first LEDs 50 that emit a larger amount of light in the direction parallel to the optical axis OA are turned on and the second LEDs 60 are turned off during regular capturing. On the other hand, the second LEDs 60 that emit a larger amount of light toward the optical axis OA of the dermoscopic camera 1 (slightly inward from the forward direction) are turned on and the first LEDs 50 are turned off during dermoscopic capturing.

The cover plate 14 comprises, for example, a light-transmissible synthetic resin. The cover plate 14 covers in front of the LED substrate 13 and has an opening 14a that opens the front of the lens unit 12. The cover plate 14 suppresses entry of foreign substances such as dirt and dust into the camera body 10 and allows light that is emitted by the first LEDs 50 and the second LEDs 60 to pass and exit forward.

(Configuration of the Attachment 40)

The attachment 40 has, as shown in FIG. 4, a cylindrical body 42 at the leading end of which a disk-like contact plate 41 is formed, an attachment ring 45 that is fixed to the outer periphery of the cylindrical body 42, a polarizing filter 23 as a polarizing member, and a cover plate 24.

The cylindrical body 42 comprises, for example, a resin such as polyvinyl chloride derivatives and acrylic resins. The cylindrical body 42 is cylindrical and has the contact plate 41 formed at the leading end. The inner periphery of the cylindrical body 42 is mirror-finished for reflecting light. The contact plate 41 is a flange-like plate that protrudes outward from the outer periphery of the cylindrical body 42. As described later, the contact plate 41 is made in contact with the skin lesion to stable the orientation of the dermoscopic camera 1 during dermoscopic capturing.

The attachment ring 45 is fixed to the outer periphery of the cylindrical body 42 and has multiple recesses 45a for the operator who captures an image to place his fingers. The operator can attach the cylindrical body 42 to the leading end of the cover part 15 by, for example, threading the attachment 40 into the cover part 15. The attachment 40 and the cover part 15 are detachable by a known method such as threading or fitting.

The polarizing filter 23 is provided in the hollow part of the attachment 40. As the attachment 40 is attached to the camera body 10, the polarizing filter 23 is placed in front of the cover plate 14. The polarizing filter 23 is situated on the optical axis OA and polarizes light that is emitted by the second LEDs 60 as the light passes through it. The polarized light is reflected by subdermal substances while its irregular reflection on the skin surface is suppressed.

The cover plate 24 comprises, for example, a glass body. The cover plate 24 is disposed in the hollow part of the cylindrical body 42 so that its front face is set back by a length L from the front face of the attachment 40 as shown in the enlarged view of FIG. 4. As a result, a circular recess 41a having a depth of the length L is formed in the front face of the attachment 40. The length L is, for example, 1 mm. The cover plate 24 allows light that has exited from the polarizing filter 23 to pass forward and reflected light from the skin lesion to enter the dermoscopic camera 1. Moreover, the cover plate 24 protects the inside of the attachment 40 from moisture and dust. Moreover, it may be possible to provide a second polarizing filter of which the polarization axis intersects with the polarizing filter 23 and make reflected light from the skin lesion that enters the dermoscopic camera 1 pass through the second polarization filter.

(Course of LED Light During Dermoscopic Capturing)

Figure 5:
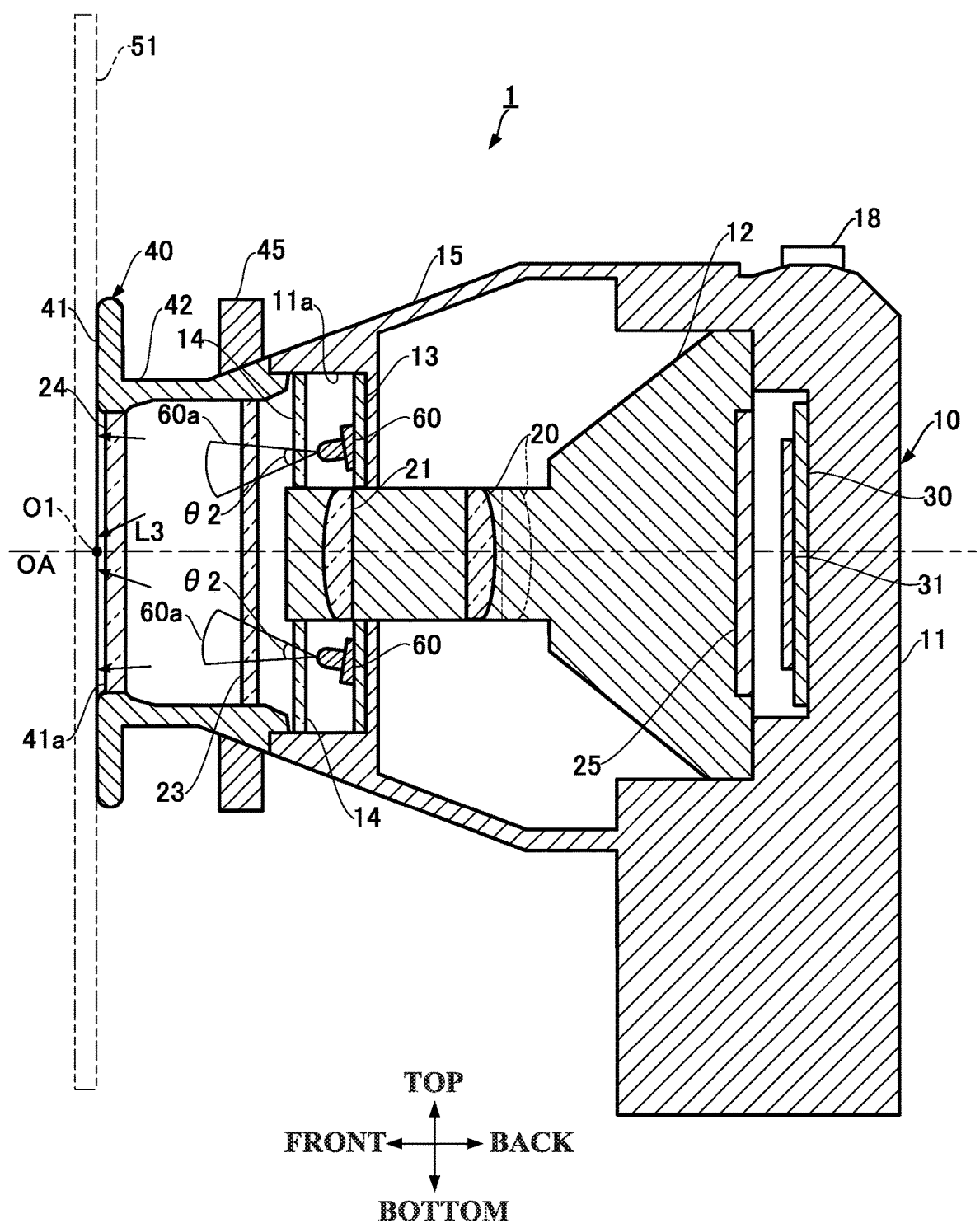
FIG. 5 is a cross-sectional view of the dermoscopic camera during dermoscopic capturing.

FIG. 5 is a cross-sectional view of the dermoscopic camera during dermoscopic capturing. During dermoscopic capturing, the second LEDs 60 are turned on and the first LEDs 50 are turned off. For the purpose of explanation, FIG. 5 shows only the second LEDs 60 that are turned on.

As shown in FIG. 5, the second LEDs 60 are tilted inward of the dermoscopic camera 1 so that the protruding direction of the bullet-like part is turned to the direction of the optical axis OA. Therefore, the second LEDs 60 emit a large amount of light primarily in a direction of approaching the optical axis OA that is the protruding direction of the bullet-like part as indicated by an emission range 60a. Here, the second LEDs 60 are LEDs having an emission angle θ2 about the emission direction L2. Light that is emitted by the second LEDs 60 passes through the cover plate 14 and the polarizing filter 23 and enters the cylindrical body 42. The light that is polarized by the polarizing filter 23 passes through the cover plate 24 and exits forward as indicated by the arrow L3 while the light is reflected in part by the mirror-finished inner periphery of the cylindrical body.

(Course of LED Light During Regular Capturing)

Figure 6:
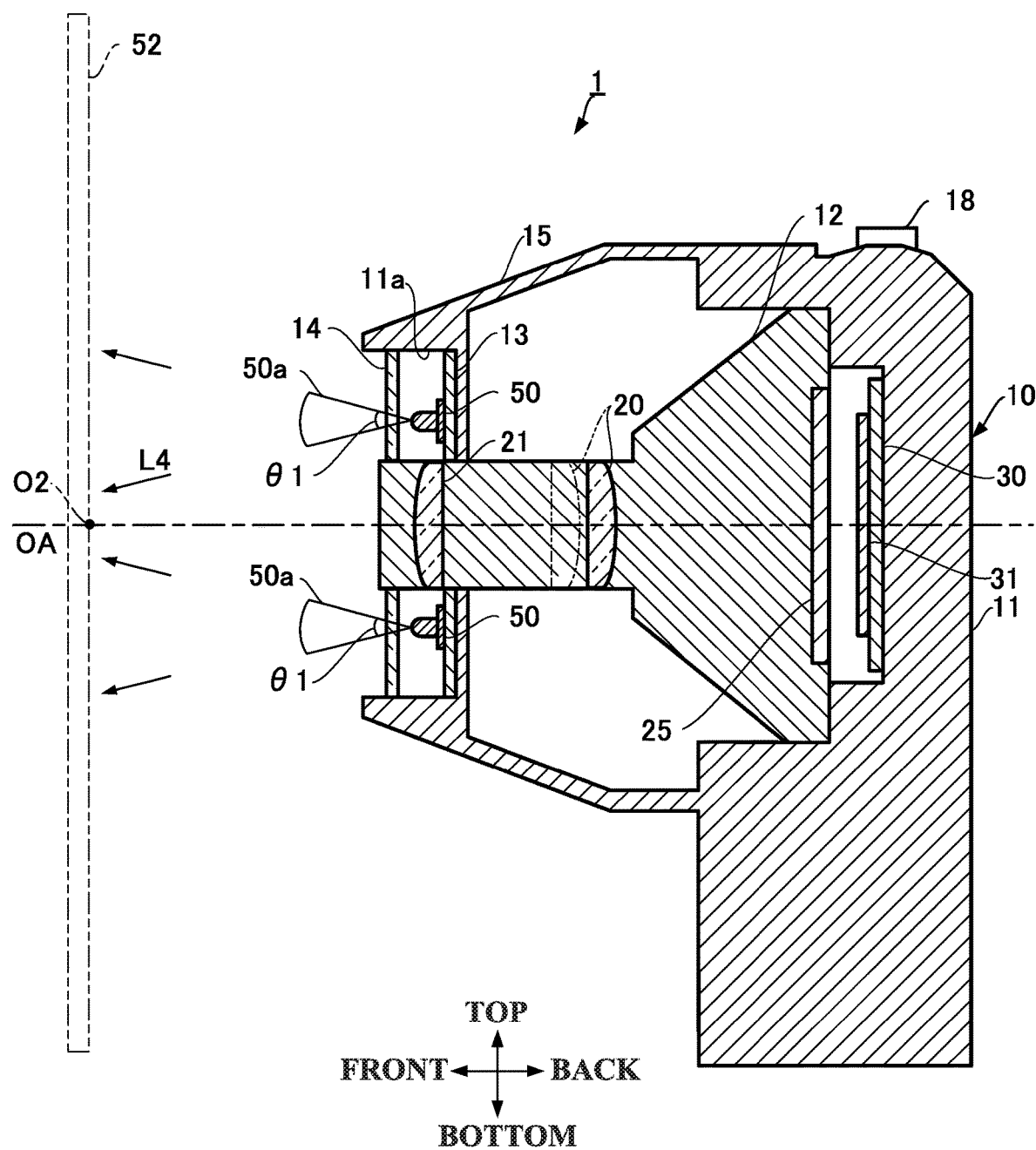
FIG. 6 is a cross-sectional view of the dermoscopic camera during regular capturing.

FIG. 6 is a cross-sectional view of the dermoscopic camera during regular capturing. The attachment 40 is detached from the camera body 10 during regular capturing. Then, the first LEDs 50 are turned on and the second LEDs 60 are turned off. For the purpose of explanation, the cross-sectional view of FIG. 6 shows only the first LEDs 50 that are turned on.

As shown in FIG. 6, the first LEDs 50 are provided with the protruding direction of the bullet-like part being the forward direction that is the direction parallel to the optical axis OA. Therefore, the first LEDs 50 emit a large amount of light primarily in the forward direction that is the direction parallel to the optical axis OA that is the protruding direction of the bullet-like part as indicated by an emission range 50a. Here, the first LEDs 50 are LEDs having an emission angle θ1 about the emission direction L1. In this embodiment, the emission angle θ1 of the first LEDs 50 and the emission angle θ2 of the second LEDs 60 are equal. Light that is emitted by the first LEDs 50 passes through the cover plate 14. The light that has passed through the cover plate 14 travels while gradually extending, and eventually illuminates the skin lesion as indicated by the arrow L4.

(Illuminance Distribution of LED Light)

Figure 7B:
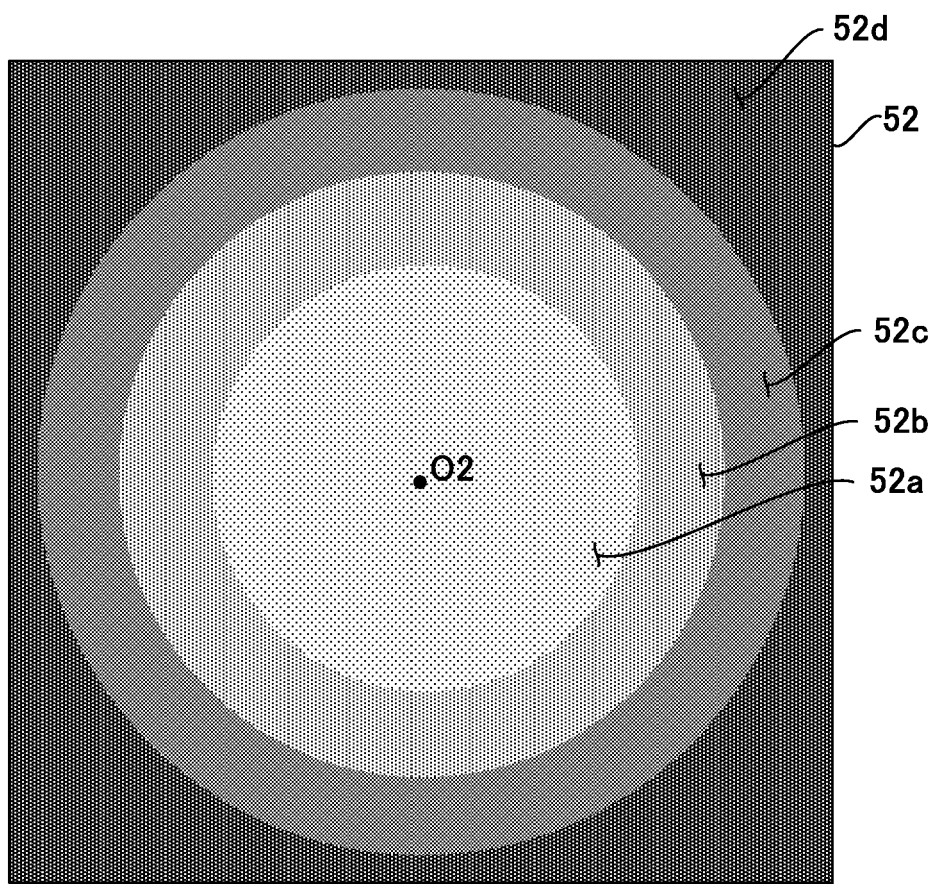
FIG. 7B is a schematic illustration that shows the illuminance distribution of light that is emitted by a light source on the illuminated surface shown in FIG. 6.

The illuminance distribution of light that is emitted by the first LEDs 50 and the second LEDs 60 that are light sources provided to the dermoscopic camera 1 will be described next. FIG. 7A is a schematic illustration that shows the illuminance distribution of light that is emitted by a light source on the illuminated surface shown in FIG. 5. Moreover, FIG. 7B is a schematic illustration that shows the illuminance distribution of light that is emitted by a light source on the illuminated surface shown in FIG. 6. Here, an illuminated surface 51 shown in FIG. 5 corresponds to the surface position of a skin lesion (an object) during dermoscopic capturing. Moreover, an illuminated surface 52 shown in FIG. 6 corresponds to the surface position of a skin lesion (an object) during regular capturing. The illuminated surface 52 is situated, for example, one meter away from the dermoscopic camera 1. Here, in FIGS. 7A and 7B, areas with higher illuminances are filled with colors closer to white. Moreover, in FIGS. 7A and 7B, for easier understanding of the disclosure, an imaginary point O1 that is the intersection between the illuminated surface 51 and an extended line of the optical axis OA and an imaginary point O2 that is the intersection between the illuminated surface 52 and an extended line of the optical axis OA are shown.

As described above, during dermoscopic capturing, the second LEDs 60 that are tilted inward are turned on and the first LEDs 50 are turned off. As shown in FIG. 5, as the second LEDs 60 are turned on, light having a specific emission angle as indicated by the emission range 60a is emitted. The emission direction is generally within the dermoscopic camera 1 and turned to a direction of approaching the optical axis OA. As a result, light that is emitted by the second LEDs 60 is collected at the center (the optical axis OA) as it travels to the front of the dermoscopic camera 1. Therefore, light that exits via the cover plate 24 (the arrow L3) is intense light as a result of light from the second LEDs 60 being collected. During dermoscopic capturing, the front face of the contact plate 41 is in contact with the skin lesion and the skin lesion is situated immediately before the cover plate 24. Therefore, as shown in FIG. 7A, an illuminated region 51a around the imaginary point O1 where intense light is emitted and an outer unilluminated region 51b where no light is emitted are formed on the illuminated surface 51 that corresponds to the surface of a skin lesion. The illuminated region 51a is nearly equal in size to the recess 41a that is formed at the leading end of the attachment 40 (FIG. 5). As described above, it is possible to emit to a skin lesion collected, intense light by the second LEDs 60 that are directed inward during dermoscopic capturing. Therefore, it is possible to emit light to subdermal substances, make the light reflected, and capture a dermoscopic image.

On the other hand, during regular capturing, the first LEDs 50 are turned on and the second LEDs 60 are turned off. As shown in FIG. 6, light from the first LEDs 50 that are provided at equal intervals on a concentric circle has a specific emission angle as indicated by the emission range 50a. Light that is emitted by the first LEDs 50 passes through the cover plate 14 and exits forward. Since the dermoscopic camera 1 and the illuminated surface 52 are spaced, for example, by one meter or so, light that is emitted by the first LEDs 50 widely extends. Therefore, a larger area is illuminated with light on the illuminated surface 52 than during dermoscopic capturing while illuminating light intensity is lower. For example, during regular capturing, as shown in FIG. 7B, an illuminated region 52a around the imaginary point O2 that is larger in area and lower in illuminance than the illuminated region 51a, an illuminated region 52b that is larger in area and lower in illuminance than the illuminated region 52a, an illuminated region 52c that is larger in area and lower in illuminance than the illuminated region 52b, and an outer unilluminated region 52d where no light is emitted are formed on the illuminated surface 52. As a result, it is possible to emit light to a large area around a skin lesion during regular capturing.

(Usage Example of the Dermoscopic Camera 1)

For conducting dermoscopic capturing with the dermoscopic camera 1, the operator attaches the attachment 40 to the leading end of the camera body 10 as shown in FIG. 5. Next, the operator presses the power button 17 to power on the dermoscopic camera 1. Subsequently, the operator operates the touch panel screen to set the dermoscopic camera 1 to the dermoscopic capturing state. As a result, the first capturing lens 20 that is movable back and forth is adjusted to the dermoscopic capturing position (the solid line position in FIG. 5) so that the skin lesion is magnified to a given magnification (for example, 10 to 30 times). Next, the operator makes the contact plate 41 contact with the skin lesion and presses the shutter button 18 halfway down. At this point, the recess 41a that is formed in the front face of the attachment 40 suppresses contact with the skin lesion. Pressing the shutter button 18 halfway down allows only the second LEDs 60 to turn on and keeps the first LEDs 50 turned off. Light that is emitted by the second LEDs 60 is polarized by the polarizing filter 23 and exits from the cover plate 24. Light that has exited from the cover plate 24 reaches under the skin while its irregular reflection on the skin lesion surface is suppressed, and is reflected by subdermal substances. The reflected light is introduced into the lens unit 12 via the cover plate 24 and the polarizing filter 23. The light that is introduced into the lens unit 12 is magnified 10 to 30 times via the second capturing lens 21 and the first capturing lens 20 and forms an image on the imaging element 31 of the camera body 10. As the shutter button 18 of the camera body 10 is pressed all the way down with any timing, a captured image that is read by the imaging element 31 is stored in the storage of the camera body 10. The captured image that is stored as just described can be used for examination and diagnosis of, for example, melanocytic nevus, melanocarcinoma, keratosis seborrheica, basal cell cancer, vascular lesions, and Bowen's disease.

For subsequently conducting regular capturing with the dermoscopic camera 1, the operator detaches the attachment 40 from the camera body 10 (FIG. 6). Next, the operator operates the touch panel screen to set the dermoscopic camera 1 to the regular capturing state. As a result, the first capturing lens 20 that is movable back and forth is adjusted to the regular capturing position (the solid line position in FIG. 6). Here, in FIG. 6, the first capturing lens 20 that is situated at the dermoscopic capturing position is indicated by a dash-dot-dot line. As shown, the first capturing lens 20 during regular capturing is placed closer to the imaging element 31 (in the back) than the first capturing lens 20 during dermoscopic capturing. As a result, the focal length can be changed and the magnification can be changed to a lower value. Then, for example, the operator presses the shutter button 18 halfway down with the dermoscopic camera 1 spaced from the skin lesion by a given distance. As a result, only the first LEDs 50 are turned on and the second LEDs 60 are kept turned off. Light that is emitted by the first LEDs 50 passes through the cover plate 14 and illuminates a large area around the skin lesion. The emitted light is reflected on the skin lesion surface, introduced into the lens unit 12, and forms an image on the imaging element 31 of the camera body 10. As the shutter button 18 of the camera body 10 is pressed all the way down with any timing, a captured image that is read by the imaging element 31 is stored in the storage of the camera body 10. As a result, it is possible to capture the skin surface condition.

Efficacy of the Embodiment

As described above, the dermoscopic camera 1 to which the present disclosure is applied comprises the second LEDs 60 that are capable of emitting light suitable for dermoscopic capturing and the first LEDs 50 that are capable of emitting light suitable for regular capturing. With such a configuration, dermoscopic capturing and regular capturing can be switched simply by selecting the LEDs to emit light. As a result, it is possible to easily switch between the dermoscopic capturing state and the regular capturing state.

Moreover, the first LEDs 50 are provided to the dermoscopic camera 1 so that a large amount of light is emitted primarily in the forward direction that is the direction parallel to the optical axis OA of the dermoscopic camera 1. As a result, light that is emitted by the first LEDs 50 during regular capturing can be emitted to a large area around the skin lesion. As a result, it is possible to emit light suitable for regular capturing.

Moreover, the second LEDs 60 are mounted on the LED substrate 13 with a tilt inward of the dermoscopic camera 1 so as to emit a large amount of light primarily in a direction of approaching the optical axis OA of the dermoscopic camera 1. As a result, light that is emitted by the second LEDs 60 is collected at the center (the optical axis OA) as it travels to the front of the dermoscopic camera 1 and it is possible to emit to the skin lesion intense light suitable for dermoscopic capturing.

Moreover, the LED substrate 13 is disposed near the second capturing lens 21 that is situated in the front of the set of lenses that is provided to the lens unit 12. Therefore, the first LEDs 50 and the second LEDs 60 are situated in the front of the camera body 10 (in the front of the dermoscopic camera 1). As a result, light that is emitted by the first LEDs 50 and the second LEDs 60 is emitted from the dermoscopic camera 1 with almost no loss in the amount of light. As a result, it is possible to brightly illuminate the skin lesion that is an object.

Moreover, the contact plate 41 for making contact with the skin lesion is formed at the leading end of the attachment 40, whereby it is possible to stable the orientation of the dermoscopic camera 1 during dermoscopic capturing. Furthermore, it is possible to fix the distance between the skin lesion and the dermoscopic camera 1. Therefore, it is possible to predetermine the positioning of the first capturing lens 20 and the second capturing lens 21 during dermoscopic capturing and thus facilitate the control of the set of lenses.

Moreover, the circular recess 41a is formed in the front face of the attachment 40. Such provision of the circular recess 41a makes it possible to capture a skin lesion that is not pressed. As a result, it is possible to obtain a dermoscopic image of a skin lesion in a natural state.

Moreover, the attachment 40 is detachably attached to the camera body 10. Therefore, it is possible to detach and easily wash the attachment 40 after dermoscopic capturing. Moreover, it is possible to prepare multiple attachments 40 and change the attachment 40 for continuously capturing different patients, whereby the examination time can be reduced. Moreover, there is no need of providing a light source to the attachment 40, whereby the attachment 40 can be simplified in configuration. This leads to reduced cost particularly where multiple attachments 40 need to be prepared.

(Other Modes)

The present disclosure is not confined to the above-described embodiment and various modifications and applications are available. In the above-described embodiment, the cover plate 14 comprises a light-transmissible material that transmits light from behind to front. However, this mode is not restrictive. For example, the cover plate 14 may have a minimally uneven surface and diffuse light that passes through the cover plate 14. As a result, it is possible to emit light to a larger area around the skin lesion during regular capturing. Moreover, it is possible to suppress unevenness in light that is emitted to the skin lesion. Moreover, during dermoscopic capturing, light that is diffused by the cover plate 14 is reflected on the inner periphery of the cylindrical body 42, whereby it is possible to emit to the skin lesion intense light suitable for dermoscopic capturing.

Moreover, in the case of dermoscopic capturing in which gel having polarization effect is applied to the skin lesion, the polarizing filter 23 that is provided to the attachment 40 can be omitted. Here, it is possible to select capturing with gel or capturing with a polarizing filter depending on the situation by preparing an attachment with the polarizing filter 23 and an attachment without the polarizing filter 23.

Moreover, in the above explanation, the first LEDs 50 and the second LEDs 60 comprise bullet-type white LEDs. However, other white LEDs may be used or other light sources may be used. Other light sources include high brightness lights such as halogen lamps, semiconductor light-emitting elements, and light-emitting elements such as organic electroluminescence. Even in such cases, the light sources that are turned on during regular capturing are directed forward and the light sources that are turned on during dermoscopic capturing are directed to the center. Furthermore, the amounts of light and/or optical characteristics of the first LEDs 50 and the second LEDs 60 may be different. For example, it may be possible that the first LEDs 50 are light sources that are capable of emitting a sufficient amount of light to reach a distant object in a large area while the second LEDs 60 are light sources that emit directional, intense light that intensively illuminates a close object although the amount of light is small.

Moreover, in the above explanation, the first LEDs 50 and the second LEDs 60 comprise LEDs that emit white light. However, ultraviolet light sources, blue light sources, or green light sources may be used. Moreover, it may be possible to provide light sources of different colors from each other as the light sources that are turned on during regular capturing and the light sources that are turned on during dermoscopic capturing, and allow the light sources of each different color to emit light independently. As a result, emission of different color light makes it possible to obtain different images and compare the obtained different images or superimpose the images, whereby examination and diagnosis of the skin lesion can be facilitated.

Moreover, in the above explanation, the first LEDs 50 are provided with the protruding direction of the bullet-like part directed forward. However, the first LEDs 50 may be provided with the protruding direction of the bullet-like part directed outward. As a result, it is possible to set the emission direction L1 to a direction of receding from the optical axis OA and emit light to a larger area during regular capturing.

Moreover, in the above-described embodiment, the first LEDs 50 for regular capturing and the second LEDs 60 for dermoscopic capturing are provided to the dermoscopic camera 1. However, it may be possible to provide a single LED or a set of LEDs to the dermoscopic camera and emit light from the provided LED or LEDs for regular capturing and dermoscopic capturing. In such a case, only provision of a configuration to change the orientation of the single LED or the set of LEDs according to the selected capturing mode is necessary.

Moreover, in the above-described embodiment, the mounting direction of the light sources for regular capturing and the mounting direction of the light sources for dermoscopic capturing are different, whereby emission of light suitable for each capturing is realized. However, it may be possible to use different light sources for regular capturing and for dermoscopic capturing and provide them in the same mounting direction. For example, it is possible to use light sources having a small emission angle (emitting light to a smaller area) as the light sources for dermoscopic capturing and use light sources having a large emission angle (emitting light to a larger area) as the light sources for regular capturing. Alternatively, it may be possible to position a reflecting plate that accompanies the LEDs differently to emit light in different directions or in different emission ranges. As a result, it is possible to emit to the skin lesion collected light during dermoscopic capturing and largely-extended light during regular capturing.

Moreover, in the above-described embodiment, the second LEDs 60 are turned on during dermoscopic capturing and the first LEDs 50 are turned on during regular capturing. However, both LEDs may be turned on during regular capturing for brighter photography.

Moreover, it may be possible to turn on the first LEDs 50 and the second LEDs 60 simultaneously, cover the first LEDs 50 to block light and allow only light from the second LEDs 60 to exit from the camera body 10 during dermoscopic capturing, and cover the second LEDs 60 to block light and allow only light from the first LEDs 50 to exit from the camera body 10 during regular capturing. Moreover, it may be possible to allow light from the first LEDs 50 and light from the second LEDs 60 to exit from the camera body 10 without covering any LEDs during regular capturing.

Moreover, it may be possible to provide the first LEDs 50 and the second LEDs 60 in a movable manner, move the second LEDs 60 to a position where light can exit from the camera body 10 and make the second LEDs 60 emit light during dermoscopic capturing, and move the first LEDs 50 to a position where light can exit from the camera body 10 and make the first LEDs 50 emit light during regular capturing. Moreover, it may be possible to move and make emit the second LEDs 60 in addition to the first LEDs 50 during regular capturing. Here, the LEDs that are not turned on have only to be on standby in the back of the camera body 10.

Moreover, in the above explanation, the contact plate 41 is made in contact with the skin lesion during dermoscopic capturing. However, if light of sufficient luminance can be emitted, dermoscopic capturing is possible with the dermoscopic camera 1 placed close to the skin lesion. In such a case, the washing after dermoscopic capturing is unnecessary and the examination time can be reduced.

Moreover, in the above explanation, the first capturing lens 20 and the second capturing lens 21 are planoconvex lenses. However, those of other modes can be used. For example, the first capturing lens 20 and the second capturing lens 21 may be any of a lens comprising a combination of two or multiple convex lenses, a single achromatic lens, and a lens comprising a combination of two or multiple achromatic lenses. Moreover, the first capturing lens 20 and the second capturing lens 21 may be aplanatic lenses or spherical lenses into which aspherical lenses are embedded. Moreover, these lenses may include an antireflection coating and/or a color filter. Moreover, in the above explanation, the lens unit 12 has a set of lenses that can change the focal length with a configuration to make the first capturing lens 20 movable. However, a configuration with a fixed focal length lens may be used.

Moreover, the medical imaging device according to the present disclosure is not confined to a medical imaging device that is capable of switching between the dermoscopic capturing state and the regular capturing state like the dermoscopic camera 1 that is described in the above embodiment. Moreover, the object is not restricted to a skin lesion. Applications include, for example, optical coherence tomography (OCT), colposcopy, and the like. Moreover, the present disclosure is also applicable to, for example, an imaging device that is capable of switching between a capturing state in which light is emitted into a hole that is formed in a structure or the like and the inside of the hole into which the light is emitted is enlarged and captured (the state in which the attachment is attached to the camera body) and a capturing state in which an area including the vicinity of the hole is captured from a position away from the hole (the state in which the attachment is detached from the camera body).

Moreover, in the above-described dermoscopic camera 1, the shutter button 18 and a touch panel screen (not shown) for executing various settings on the dermoscopic camera 1 are provided to the camera body 10. However, it may be possible to provide the shutter button 18 and an operation receiver such as a touch panel screen (not shown) to an operation unit that is physically separated from the camera body. The camera body and the operation unit are bidirectionally communicable using existing communication techniques. The operator can conduct various settings on the camera body and shutter operation by operating the operation unit.

Moreover, in the above-described dermoscopic camera 1, the attachment 40 is detachably attached to the camera body 10. However, the attachment 40 may be attached to the camera body 10 movably or the camera body 10 and the attachment 40 may be inseparable.

Embodiment 2

Figure 8:
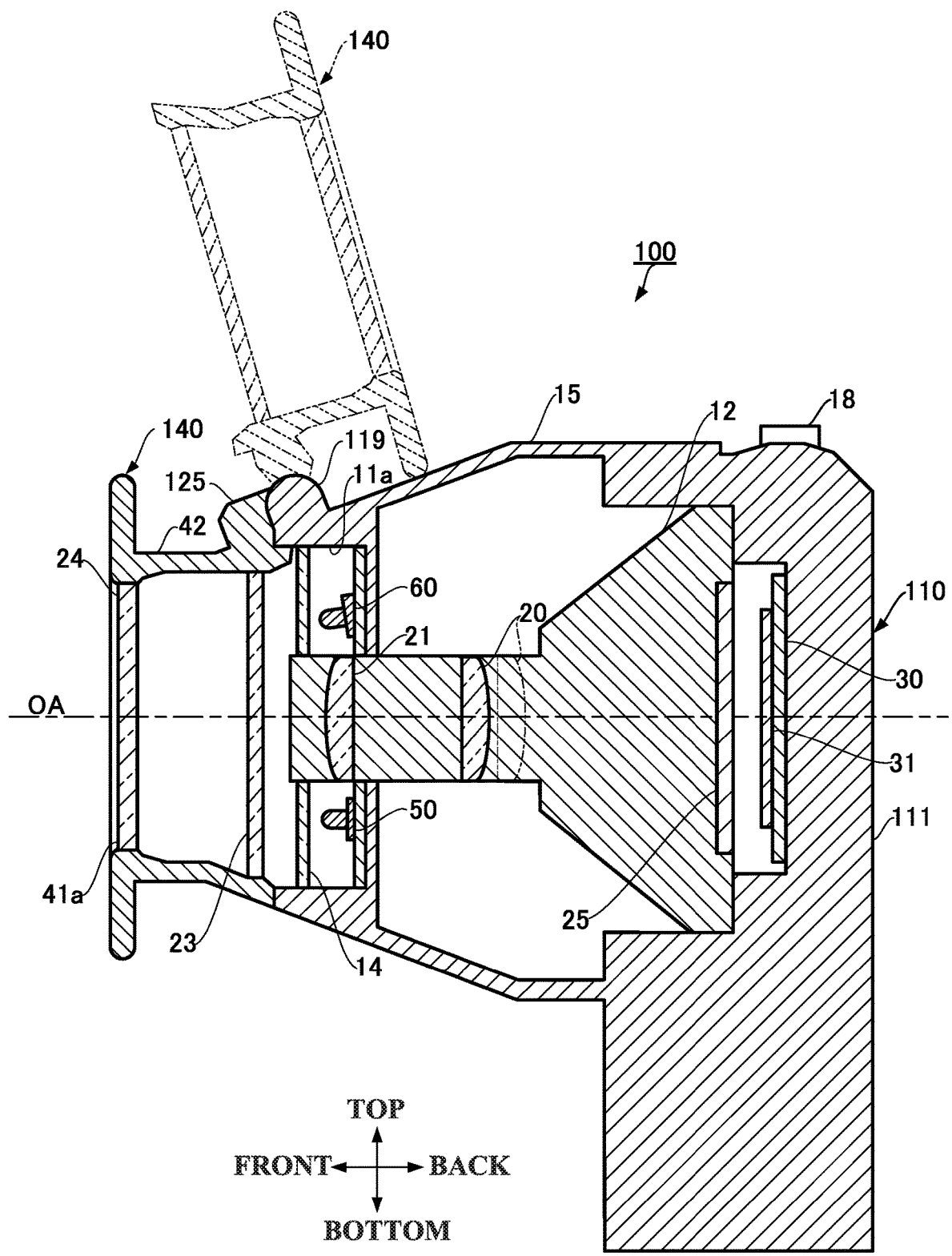
FIG. 8 is a cross-sectional view of a dermoscopic camera of Embodiment 2 to which the present disclosure is applied during dermoscopic capturing.

Embodiment 2 in which the attachment is movably attached to the camera body will be described next. FIG. 8 is a cross-sectional view of a dermoscopic camera of Embodiment 2 to which the present disclosure is applied during dermoscopic capturing. In a dermoscopic camera 100, an attachment 140 is rotatably attached to a camera body 110. A rotative supporter 119 that rotatably supports the attachment 140 is formed in an upper part of the camera body 110. A rotative protrusion (not shown) that serves as the rotation axis of the attachment 140 is formed on each of the right and left faces of the rotative supporter 119. As a rotator 125 of the attachment 140 is supported by the rotative protrusions (not shown), the attachment 140 can rotate with respect to the camera body 110. Here, although not provided with the attachment ring 45 (FIG. 1), the dermoscopic camera 100 is the same in other configurations as the dermoscopic camera 1 that is described in the above embodiment. Therefore, the same components are referred to by the same reference numbers in FIG. 8.

The operator positions the attachment 140 in front of the camera body 110 during dermoscopic capturing as shown in FIG. 8. On the other hand, the operator rotates the attachment 140 upward and opens the front of the camera body 110 during regular capturing. As just stated, it is possible to switch between the dermoscopic capturing state and the regular capturing state by rotating the attachment 140.

Moreover, the mode of moving the attachment may be not only by rotating as described above but also by sliding the attachment with respect to the camera body. It may be possible to position the attachment to cover the front of the camera body for dermoscopic capturing and slide the attachment to move from the front of the camera body for regular capturing.

Embodiment 3

Moreover, in the above-described embodiment, the light sources for regular capturing and the light sources for dermoscopic capturing are provided on the same plane (the same LED substrate 13). However, the layout of light sources is not restricted thereto. The light sources may be situated at different points in the front-back direction. A dermoscopic camera 200 of Embodiment 3 in which the light sources for regular capturing are provided behind the light sources for dermoscopic capturing will be described next. Here, in the dermoscopic camera 200, visible light LEDs 211, visible light LEDs 212, and near-infrared LEDs 215 are provided as the light sources for dermoscopic capturing. The near-infrared LEDs 215 may be replaced with ultraviolet LEDs.

Figure 9:
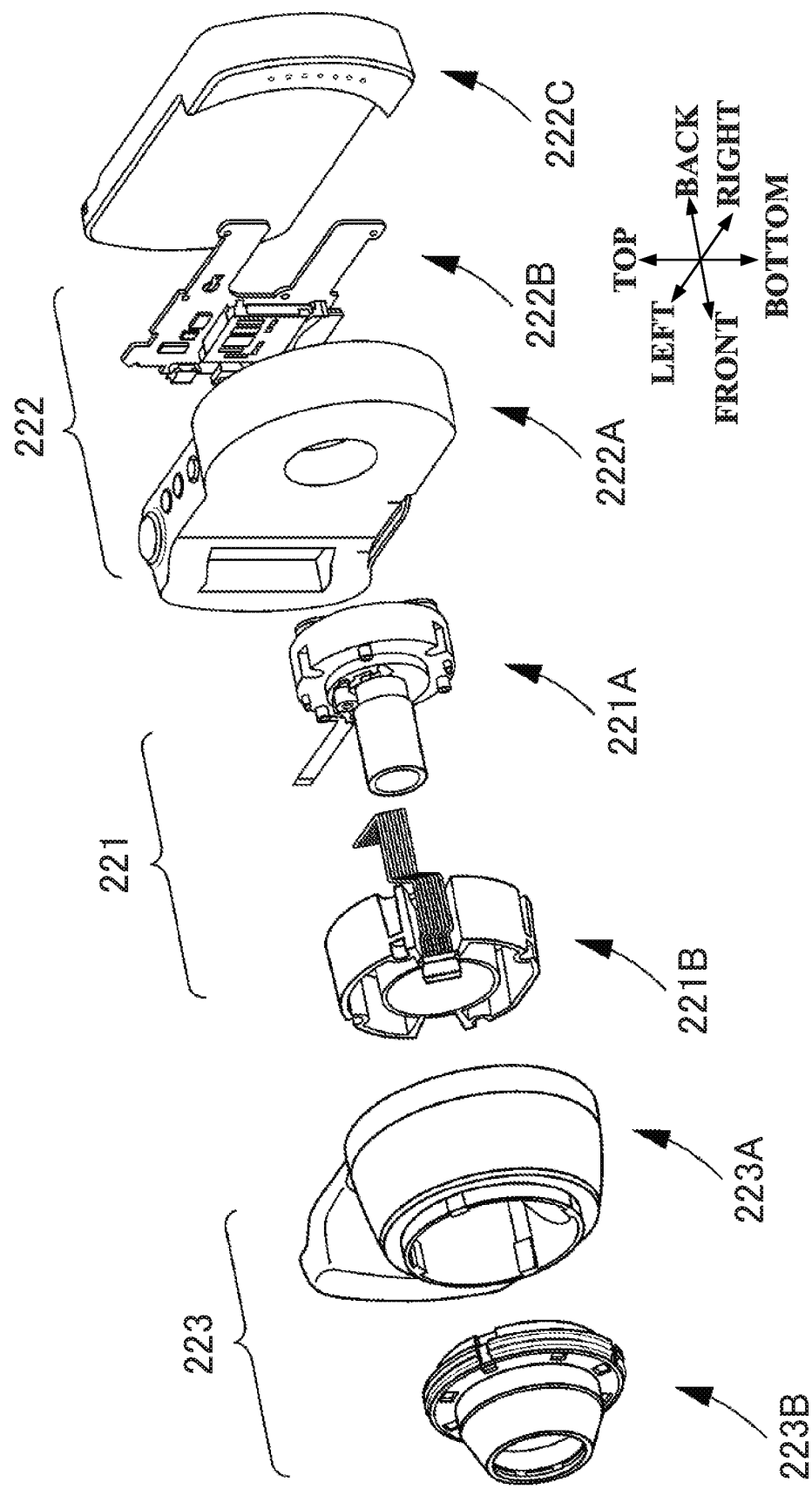
FIG. 9 is an exploded, perspective view of a dermoscopic camera of Embodiment 3 to which the present disclosure is applied.
Figure 10:
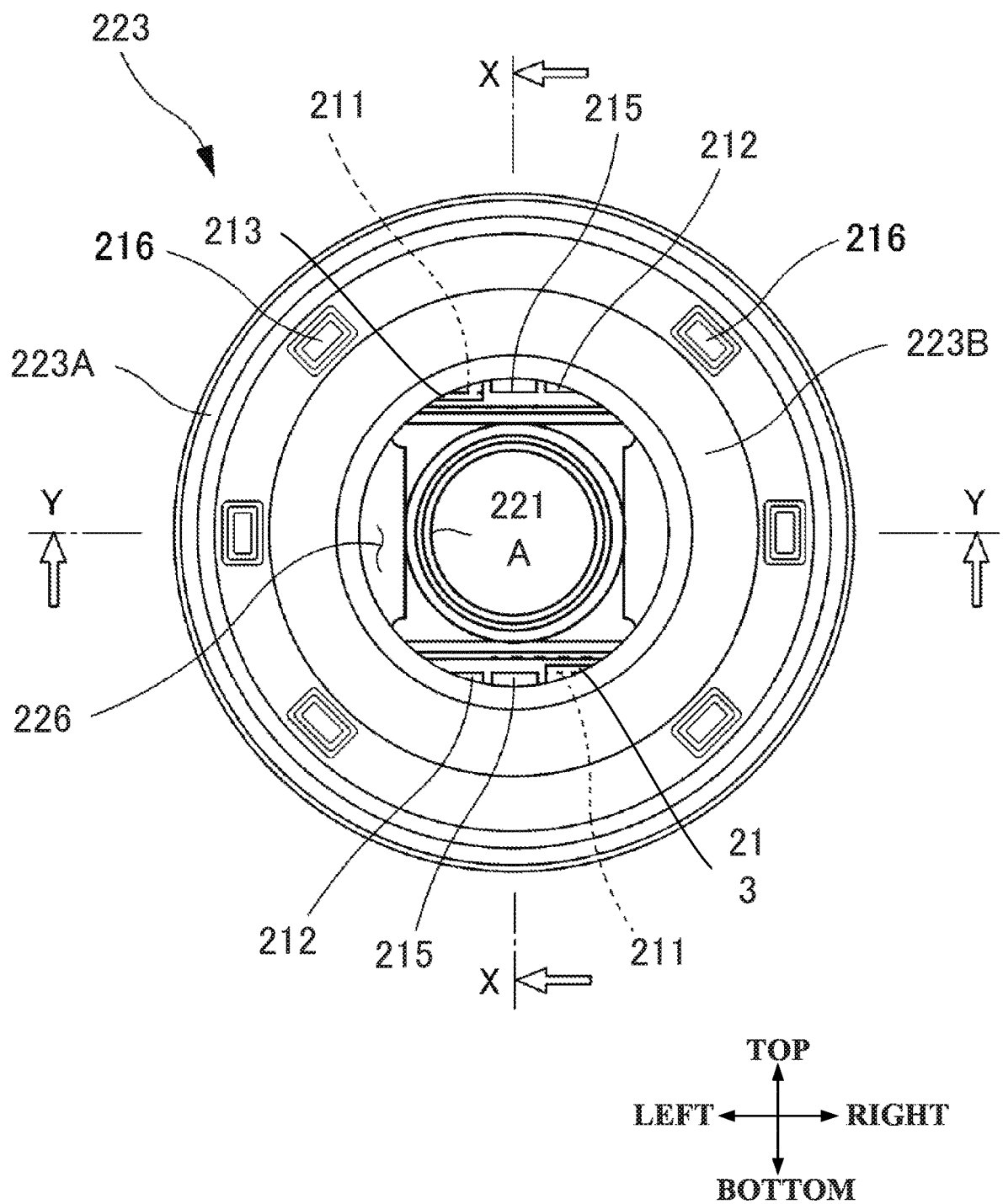
FIG. 10 is a front view of the light unit in FIG. 9.
Figure 11:
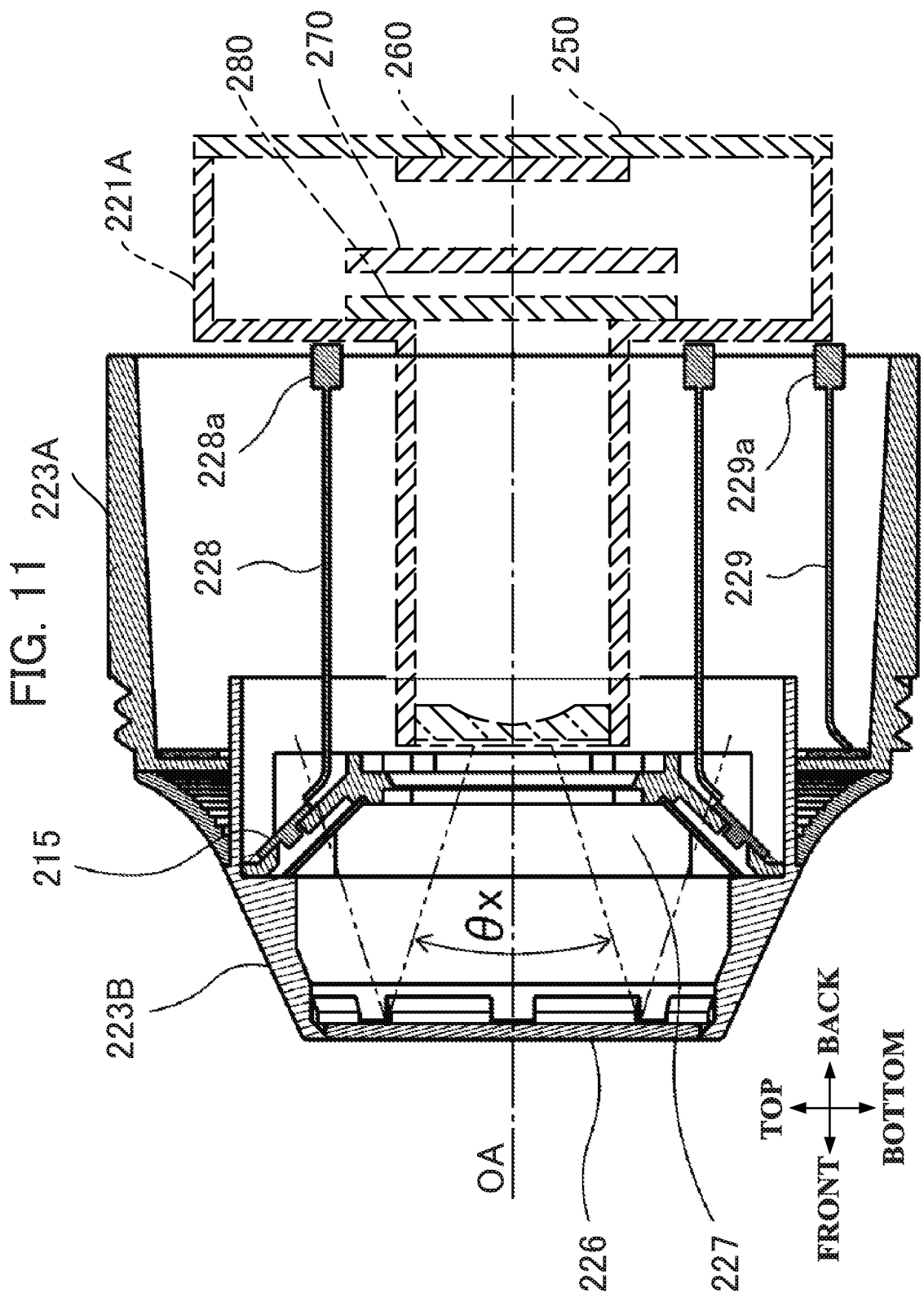
FIG. 11 is a cross-sectional view at a line X-X in FIG. 10.
Figure 12:
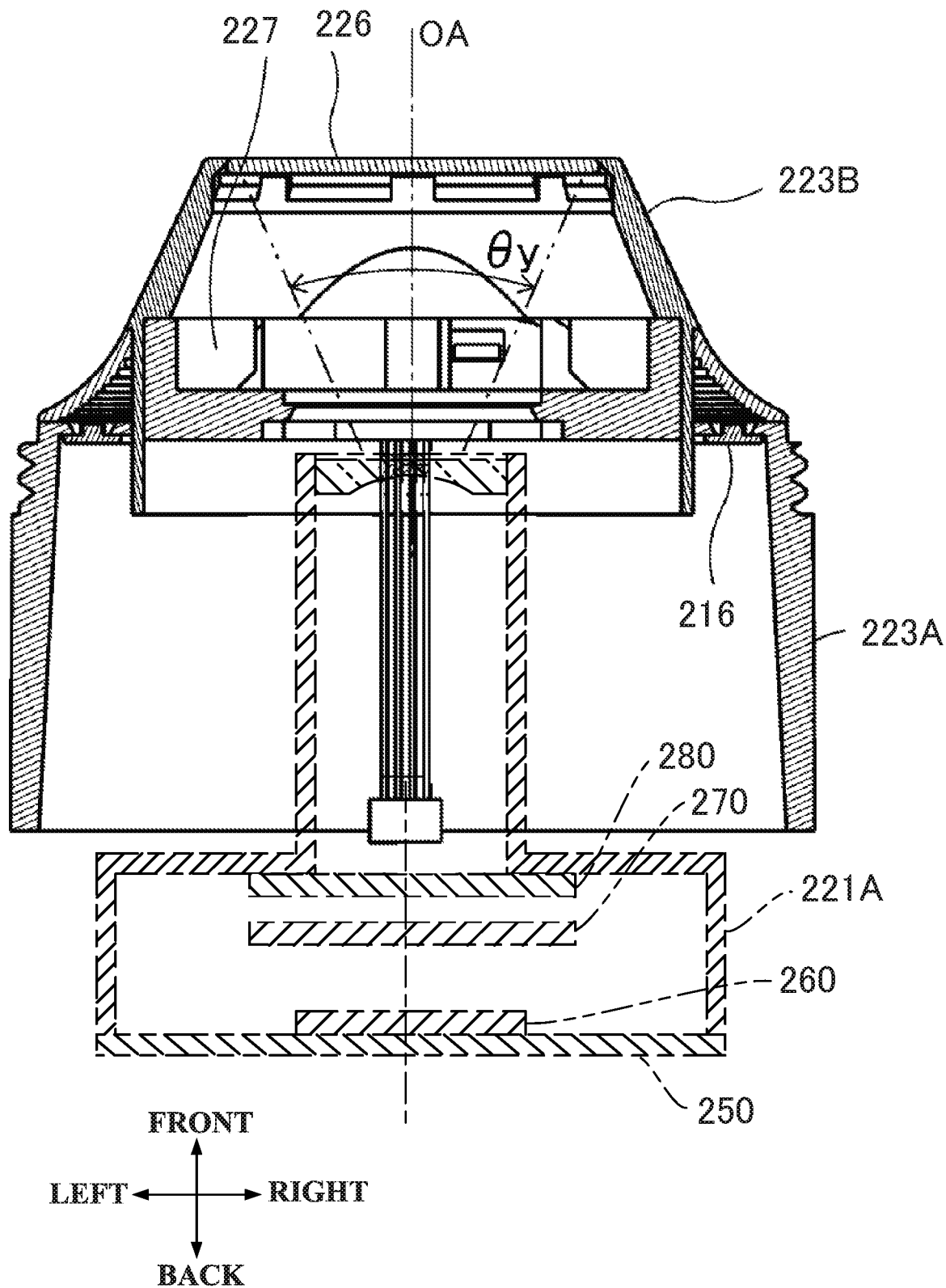
FIG. 12 is a cross-sectional view at a line Y-Y in FIG. 10.
Figure 13:
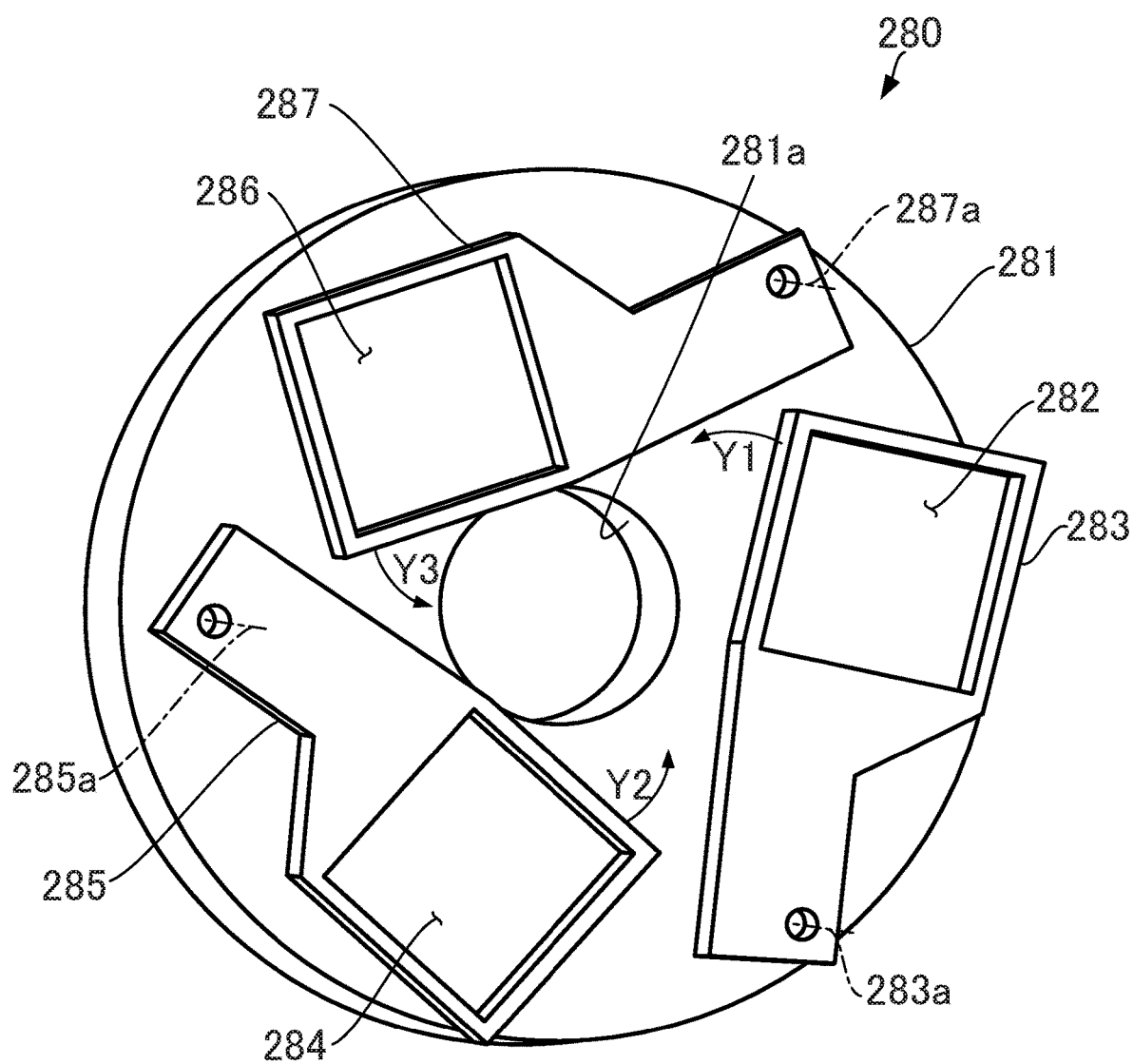
FIG. 13 is a perspective view of the filter unit in FIGS. 11 and 12.

FIG. 9 is an exploded, perspective view of a dermoscopic camera of Embodiment 3 to which the present disclosure is applied. FIG. 10 is a front view of the light unit in FIG. 9. FIG. 11 is a cross-sectional view at a line X-X in FIG. 10. FIG. 12 is a cross-sectional view at a line Y-Y in FIG. 10. FIG. 13 is a perspective view of the filter unit in FIGS. 11 and 12.

As shown in FIG. 9, the dermoscopic camera 200 (a medical imaging device) monolithically comprises a camera body 221, a light unit 223 that is provided in front of the camera body 221, and a controller 222 that is provided behind the camera body 221. The camera body 221 includes a lens unit 221A and a frame 221B. The light unit 223 includes a first cover 223A and a second cover 223B. The controller 222 includes a body 222A, a circuit substrate 222B, and a display 222C.

As shown in FIGS. 10 and 12, LEDs 216 for regular capturing are disposed annularly around the base end (in the back) of the second cover 223B and face front. In FIG. 10, a total of six, three on the right and three on the left, LEDs 216 for regular capturing are disposed by way of example.

The LEDs 216 for regular capturing are disposed at equal intervals on a concentric circle about the center of the second cover 223B. The LEDs 216 function as a ring flash that emits light forward from the peripheral positions of the lens unit 221A. The LEDs 216 comprise LEDs that emit white light. A cover member 226 is fitted in the opening at the leading end of the second cover 223B and makes contact with the skin lesion that is an object during dermoscopic capturing.

Here, in the above-described embodiment, only one kind of second LEDs 60 (FIG. 2) are provided as the light sources for dermoscopic capturing. On the other hand, in the dermoscopic camera 200, three different kinds of light sources, the LEDs 211 that emit visible light, the LEDs 212 that emit visible light, and the LEDs 215 that emit near-infrared light, are provided as the light sources for dermoscopic capturing. These light sources are disposed as a pair in the vertical direction as shown in FIG. 10. Of the pair of light sources, the upper light sources are directed diagonally downward and emit a larger amount of light in a direction of approaching the optical axis OA. On the other hand, the lower light sources are directed diagonally upward and emit a larger amount of light in a direction of approaching the optical axis OA. Moreover, the pair of LEDs 211 is covered by polarizing filters 213 while the pair of LEDs 212 is not covered by polarizing filters. Moreover, the LEDs 211, the LEDs 212, the LEDs 215 for dermoscopic capturing are provided in front of the LEDs 216 for regular capturing.

The camera body 221 is attached to the first cover 223A via the frame 221B that surrounds and supports the lens unit 221A. A circuit wiring substrate 250 and an imaging element 260 are housed in the back of the lens unit 221A as shown in FIGS. 11 and 12 and a shutter 270 and a filter unit 280 are provided in the front of the circuit wiring substrate 250 and the imaging element 260.

The filter unit 280 comprises, as shown in FIG. 13, a base plate 281, a first rotator 283 that has an infrared cut filter (IRCF) 282, a second rotator 285 that has a polarizing filter 284, and a third rotator 287 that has a near-infrared transmission filter 286. The polarization axis of the polarizing filter 284 is perpendicular to the polarization axis of the polarizing filters 213 that cover the pair of LEDs 211. The filter unit 280 is mounted on the lens unit 221A via the base plate 281. A circular light transmission hole 281a is formed at the center of the base plate 281. The base plate 281 is provided so that the center of the light transmission hole 281a coincides with the optical axis OA of the dermoscopic camera 200 (FIGS. 11 and 12). As a result, reflected light that has entered the lens unit 221A passes through the light transmission hole 281a and reaches the imaging element 260 (FIGS. 11 and 12). Here, the near-infrared transmission filter 286 is replaced with an ultraviolet transmission filter when the near-infrared LEDs 215 shown in FIG. 10 are replaced with ultraviolet LEDs.

The first rotator 283 is mounted on the base plate 281 rotatably about a rotation axis 283a. The first rotator 283 changes between a first state shown in FIG. 13 and a second state in which the infrared cut filter 282 covers the light transmission hole 281a after rotating in the arrowed direction Y1 from the first state. The second rotator 285 is mounted on the base plate 281 rotatably about a rotation axis 285a. The second rotator 285 changes between a first state shown in FIG. 13 and a second state in which the polarizing filter 284 covers the light transmission hole 281a after rotating in the arrowed direction Y2 from the first state. The third rotator 287 is mounted on the base plate 281 rotatably about a rotation axis 287a. The third rotator 287 changes between a first state shown in FIG. 13 and a second state in which the near-infrared transmission filter 286 covers the light transmission hole 281a after rotating in the arrowed direction Y3 from the first state. The first rotator 283, the second rotator 285, and the third rotator 287 are situated at different points in the front-back direction and thus can rotate independently. Therefore, it is possible to cover the light transmission hole 281a with a single filter or with multiple filters.

Here, the reason that the configuration to emit near-infrared light and ultraviolet light in addition to dermoscopic capturing with visible light is preferable for diagnosis of a skin lesion is as follows. Dermoscopic capturing with near-infrared light is suitable for capturing the deepest part of a skin (dermis) and light of the shorter wavelengths tends to fail to reach the deeper parts. Moreover, melanin in pigment disorders and hemoglobin in angioma can be pigments that cause change in color tone in a skin lesion. However, emission of visible light is suitable for oxyhemoglobin of the latter while ultraviolet light that has shorter wavelengths than visible light is more effective for dopamelanin of the former, which is poor in absorption of light of longer wavelengths.

This embodiment makes it possible to turn on the LEDs 211, the LEDs 212, the LEDs 215, and the LED 216 in four different patterns. In other words, a first pattern to turn on a pair of upper and lower near-infrared (or ultraviolet) LEDs 215, a second pattern to turn on a pair of upper and lower visible light LEDs 211 that are covered with the polarizing filters 213, a third pattern to turn on a pair of upper and lower visible light LEDs 212 that are not covered with the polarizing filters 213, and a fourth pattern to turn on the LEDs 216 for regular capturing. Moreover, it is possible to easily switch to a different capturing state by controlling the rotative operation of the first rotator 283, the second rotator 285, and the third rotator 287 according to the above turn-on patterns.

It is also possible to conduct capturing in the above different capturing states at a time with a single shutter operation. For example, it is possible to conduct automatic, successive capturing in a random order of the first through third patterns that are used for dermoscopic capturing. Furthermore, it is also possible to conduct automatic, successive capturing including the fourth pattern for regular capturing.

FIG. 11 shows a vertical field angle θx in dermoscopic capturing with the first through third patterns. In the vertical direction, the LEDs 215, the LEDs 211, or the LEDs 212 emit light that is tapered toward the optical axis OA. As a result, the vertical field angle θx at which light that is reflected on the skin lesion that is in contact with the cover member 226 enters the lens unit 221A is relatively small. For example, the vertical field angle θx is 35.2° in FIG. 11.

Here, in FIG. 11, a pair of upper and lower wires 228 and terminals 228a for passing control signals to the LEDs 215 (including the LEDs 211 and the LEDs 212) is provided. Moreover, a wire 229 and a terminal 229a for passing control signals to the LEDs 216 shown in FIG. 12 are provided near the outer periphery of the first cover 223A.

FIG. 12 shows a horizontal field angle θy in dermoscopic capturing with the first through third patterns. In the horizontal direction, the LEDs 215, the LEDs 211, or the LEDs 212 emit light in parallel to the optical axis OA. As a result, the horizontal field angle θy at which light that is reflected on the skin lesion that is in contact with the cover member 226 enters the lens unit 221A is relatively large. For example, the horizontal field angle θy is 47° in FIG. 12.

Efficacy of Embodiment 3

As described above, the dermoscopic camera 200 according to Embodiment 3 makes it possible to obtain, with a simple configuration and operation, an image in a condition enabling observation of the skin surface under emission of the unpolarized LEDs 212, an image in a condition enabling observation of the inner skin part under emission of the polarized LEDs 211, an image in a condition enabling observation of the skin surface under emission of the LEDs 215 that emit near-infrared light (or ultraviolet light), and an image in a condition enabling observation of the skin surface under emission of the LEDs 216 that emit ordinary white light. Moreover, the filter for light that passes through the lens unit 221A to pass through can be switched by controlling the operation of the filter unit 280, whereby it is possible to switch to a desired capturing state.

Moreover, provision of a polarizing plate that transmits light during dermoscopic capturing to the camera body makes unnecessary the attachment that is used in dermoscopic capturing. As a result, it is possible to eliminate the task of attaching/detaching the attachment and thus easily switch the capturing state.

The LEDs for dermoscopic capturing can be of a visible light type, of an ultraviolet type, and of a near-infrared light type. As a result, it is possible to conduct capturing using three different kinds of light sources with a single shutter operation.

Moreover, since successive capturing while switching to different capturing states is possible, the captured images are not affected by outside light change and/or slight differences in the camera such as AE and white balance. Moreover, since capturing with the same field angle and the same magnification under genuine, polarized/unpolarized light is possible, the diagnosis time can be reduced and captured images that are easy to compare are obtainable.

In the above-described embodiment, the first light sources and the second light sources are separately present. However, it is possible to make, for example, the positions and emission directions of LEDs or polarizing plates changeable and use the same light sources in the first capturing state and in the second capturing state.

Several embodiments and their modified embodiments are described above. A medical imaging device can be configured by combining the features that are described in those as appropriate. Additionally, specific details such as the configurations presented in the above-described embodiments can be changed as appropriate to the extent of not departing from the gist of the present disclosure.

The foregoing describes some example embodiments for explanatory purposes. Although the foregoing discussion has presented specific embodiments, persons skilled in the art will recognize that changes may be made in form and detail without departing from the broader spirit and scope of the invention. Accordingly, the specification and drawings are to be regarded in an illustrative rather than a restrictive sense. This detailed description, therefore, is not to be taken in a limiting sense, and the scope of the invention is defined only by the included claims, along with the full range of equivalents to which such claims are entitled.

What is claimed is:

1. A medical imaging device that includes a first capturing state for capturing a lesion in a regular capturing state and a second capturing state for capturing a lesion in a capturing state that is different from the regular capturing state and captures an image for assisting in diagnosis of the lesion, the medical imaging device comprising:
    a first light source;
    a second light source; and
    an imaging element,
    wherein:
    at least the first light source is used as a light source that emits light to an object in the first capturing state, and at least the second light source is used as a light source that emits light to the object in the second capturing state,
    an emission direction of the first light source is set to a direction that is parallel to or recedes from an optical axis,
    an emission direction of the second light source is set to a direction that approaches the optical axis, and
    the emission direction of the first light source and the emission direction of the second light source are set such that an illuminated region that is illuminated with the light emitted from the second light source to the object in the second capturing state is smaller than an illuminated region that is illuminated with the light emitted from the first light source to the object in the first capturing state.

2. The medical imaging device according to claim 1, further comprising:
    an imaging device body comprising the first light source, the second light source, the imaging element, and a set of lenses that are situated on the optical axis, the optical axis connecting the imaging element and the object.

3. The medical imaging device according to claim 2, wherein:
    the first capturing state is the regular capturing state,
    the second capturing state is a dermoscopic capturing state, and
    the set of lenses functions as a magnifying lens in the dermoscopic capturing state and functions as a wide-angle lens that has a wider angle in the regular capturing state than in the dermoscopic capturing state.

4. The medical imaging device according to claim 3, wherein the imaging device body further comprises a polarizing member that is situated on the optical axis and is used for polarizing light that is emitted by the second light source for dermoscopic capturing.

5. The medical imaging device according to claim 2, wherein the first light source and the second light source are provided in a front of the imaging device body.

6. The medical imaging device according to claim 2, wherein:
    at least a portion of the second light source is provided with a polarizing member so as to emit polarized light from the at least the portion of the second light source,
    the first light source emits unpolarized light, and
    a polarizing member of which a polarization axis direction is different from a polarization axis direction of the polarizing member is provided in front of the imaging element.

7. The medical imaging device according to claim 2, wherein the first light source and the second light source are provided around the set of lenses.

8. The medical imaging device according to claim 1, wherein the first light source is provided behind the second light source.

9. The medical imaging device according to claim 1, wherein:
- at least a portion of the second light source is provided with a polarizing member so as to emit polarized light from the at least the portion of the second light source, and
- the first light source emits unpolarized light.

10. The medical imaging device according to claim 1, wherein the first light source is turned on in the first capturing state and both the first light source and the second light source are turned on in the second capturing state.

11. The medical imaging device according to claim 1, wherein a wavelength of the first light source is different from a wavelength of the second light source.

12. The medical imaging device according to claim 1, wherein the first light source and the second light source are composed of one light source, and are configured to, between the first capturing state and the second capturing state, change a light emission direction.

13. A medical imaging device that includes a first capturing state for capturing a lesion in a regular capturing state and a second capturing state for capturing a lesion in a capturing state that is different from the regular capturing state and captures an image for assisting in diagnosis of the lesion, the medical imaging device comprising:
- an imaging device body;
- a first light source;
- a second light source;
- an imaging element; and
- a set of lenses, wherein:
- at least the first light source is used as a light source that emits light to an object in the first capturing state which is the regular capturing state, and at least the second light source is used as a light source that emits light to the object in the second capturing state which is a dermoscopic capturing state,
- an emission direction of the second light source is set to a direction that is different from an emission direction of the first light source,
- the first light source, the second light source, the imaging element, and the set of lenses are provided in the imaging device body, the set of lenses being situated on an optical axis that connects the imaging element and the object,
- the emission direction of the second light source is set to a direction of approaching the optical axis, and
- the set of lenses functions as a magnifying lens in the dermoscopic capturing state and functions as a wide-angle lens that has a wider angle in the regular capturing state than in the dermoscopic capturing state.

* * * * *